(12) United States Patent
Ansmann et al.

(10) Patent No.: US 6,878,379 B2
(45) Date of Patent: Apr. 12, 2005

(54) COSMETIC PREPARATIONS

(75) Inventors: Achim Ansmann, Erkrath (DE); Bernd Fabry, Korschenbroich (DE)

(73) Assignee: Cognis Deutschland GmbH & Co., KG, Duesseldorf (DE)

( * ) Notice: Subject to any disclaimer, the term of this patent is extended or adjusted under 35 U.S.C. 154(b) by 239 days.

(21) Appl. No.: 09/931,670

(22) Filed: Aug. 16, 2001

(65) Prior Publication Data

US 2002/0012686 A1 Jan. 31, 2002

Related U.S. Application Data

(62) Division of application No. 09/308,084, filed as application No. PCT/EP97/06086 on Nov. 4, 1997, now Pat. No. 6,365,168.

(30) Foreign Application Priority Data

Nov. 13, 1996 (DE) .......................................... 196 46 869

(51) Int. Cl.⁷ .............................. A61K 6/00; A61K 7/00
(52) U.S. Cl. ...................... 424/401; 424/400; 424/70.1; 424/78.02
(58) Field of Search ................................. 424/400, 401, 424/47, 59, 63, 70.1, 78.02, 78.08; 524/747

(56) References Cited

U.S. PATENT DOCUMENTS 6,309,628 B1 * 10/2001 Ansmann et al. ......... 424/70.12
6,365,168 B1 * 4/2002 Ansmann et al. ........... 424/401

\* cited by examiner

*Primary Examiner*—Dameron L. Jones
(74) *Attorney, Agent, or Firm*—Aaron R. Ettelman; Steven J. Trzaska; Daniel S. Ortiz

(57) ABSTRACT

A pearlescent composition containing: (a) a dialkyl ether corresponding to formula (I):

$$R^1\text{—}O\text{—}R^2 \qquad (I)$$

wherein $R^1$ and $R^2$ independently of one another represent linear or branched alkyl and/or alkenyl groups having from 12 to 22 carbon atoms; (b) a cationic polymer; and (c) an emulsifier selected from the group consisting of a fatty acid-N-alkyl polyhydroxyalkyl amide, an alkyl ether sulfate, a betaine, and mixtures thereof.

8 Claims, No Drawings

COSMETIC PREPARATIONS

CROSS-REFERENCE TO RELATED APPLICATIONS

This is a divisional of application Ser. No. 09/308,084, filed May 12, 1999 now U.S. Pat. No. 6,365,168 which is a 371 of PCT/EP97/06086 filed Nov. 4, 1997.

BACKGROUND OF THE INVENTION

This invention relates to cosmetic formulations containing (a) selected pearlescent waxes, (b) cationic polymers and (c) selected emulsifiers and to the use of the mixtures for the production of pearlescent conditioning shampoos.

Up to 15 years ago, hair shampoos generally consisted solely of water and surfactants which was undoubtedly quite adequate so far as the cleaning and degreasing of the hair was concerned. With the enlightenment of consumers as to the risks involved in handling cosmetic ingredients and with the demand for products which not only clean, but also have a caring effect, the requirements which modern cosmetic formulations in general and hair shampoos in particular are expected to satisfy have steadily become more stringent. The consumer justifiably expects the products to show maximum dermatological compatibility, i.e. irritation of the skin and mucous membrane should be reliably avoided, even in the event of frequent use by particularly sensitive people. So far as personal care is concerned, the formulations are also expected to improve the combability of hair, i.e. to have a conditioning and antistatic effect. Finally, it has been found that the appearance of the formulations, i.e. for example a brilliant pearlescence, has a positive effect on consumers interested in buying them.

For the reasons mentioned, modern hair shampoos often contain mild surfactants, pearlescent waxes, for example ethylene glycol bis-stearate, and cationic polymers with conditioning properties. Unfortunately, the formulation possibilities of these products are limited because cationic polymers have only limited solubility in aqueous solutions so that either only small quantities can be used or the appearance of the product suffers and its pearlescence loses brilliance through the precipitation of the polymers. An overview of modern pearlescent formulations was published by A. Ansmann et al. in Parf. Kosm. 75, 578 (1994).

Pearlescent concentrates containing acylated ethylene glycols as pearlescent waxes together with alkyl glucosides are known, for example, from European patents EP-B1 0 376 083 and EP-B1 0 570 398 (Henkel). Compositions containing alkyl oligoglycosides and cationic polymers are known from European patent EP-B1 0 377 354 (Kao).

Accordingly, the complex problem addressed by the present invention was to provide new cosmetic formulations, more particularly pearlescent conditioning shampoos, which would be distinguished by brilliant pearlescence, high stability in storage, excellent conditioning properties and particular dermatological compatibility.

DESCRIPTION OF THE INVENTION

The present invention relates to cosmetic formulations containing
(a) dialkyl ethers corresponding to formula (I):

$$R^1—O—R^2 \quad (I)$$

in which $R^1$ and $R^2$ independently of one another represent linear or branched alkyl and/or alkenyl groups containing 12 to 22 carbon atoms, (b) cationic polymers and
(c) emulsifiers selected from the group consisting of alkyl and/or alkenyl oligoglycosides, fatty acid-N-alkyl polyhydroxyalkylamides, alkyl ether sulfates and/or betaines.

It has surprisingly been found that, by selecting suitable pearlescent waxes and emulsifiers, it is possible to obtain mixtures which are capable of stabilizing cationic polymers in aqueous formulations, more particularly hair shampoos, so that the products have the necessary stability in storage. At the same time, the cooperation of the distearyl ethers with the cationic polymers results in a synergistic improvement both in the pearlescent effect and in the conditioning properties. The invention includes the observation that the mixtures also show particularly advantageous dermatological compatibility.

Dialkyl Ethers

Dialkyl ethers suitable as pearlescent component (a) are normally prepared by condensation of corresponding fatty alcohols (Bull. Soc. Chim. France 333 (1949)]. Typical examples are dilauryl ether, dimyristyl ether, dicetyl ether, diisostearyl ether, dioleyl ether, dibehenyl ether and dierucyl ether. Distearyl ether is preferably used. The pearlescent waxes may have an average particle size of 0.1 to 20 µm, preferably 5 to 15 µm and more preferably 12 to 14 µm.

Cationic Polymers

Suitable cationic polymers are, for example, cationic cellulose derivatives such as, for example, the quaternized hydroxyethyl cellulose available under the name of Polymer JR 400® from Amerchol, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides, such as, for example, Lauryldimonium Hydroxypropyl Hydrolyzed Collagen (Lamequat®L Grünau), quaternized wheat polypeptides, polyethyleneimine, cationic silicone polymers such as, for example, Amidomethicone, copolymers of adipic acid and dimethyl aminohydroxypropyl diethylenetriamine (Cartaretine®, Sandoz), copolymers of acrylic acid with dimethyl diallyl ammonium chloride (Merquat® 550, Chemviron), polyaminopolyamides as described, for example, in FR-A 22 52 840 and crosslinked water-soluble polymers thereof, cationic chitin derivatives such as, for example, quaternized chitosan, optionally in microcrystalline distribution, condensation products of dihaloalkyls such as, for example, dibromobutane with bis-dialkylamines such as, for example, bis-dimethylamino-1,3-propane, cationic guar gum such as, for example, Jaguar® CBS, Jaguar® C-17, Jaguar® C-16 of Celanese, quaternized ammonium salt polymers such as, for example, Mirapol® A-15, Mirapol® AD-1, Mirapol® AZ-1 of Miranol.

Alkyl and/or Alkenyl Oligoglycosides

Alkyl and alkenyl oligoglycosides suitable as emulsifier component (c) are known nonionic surfactants which correspond to formula (II):

$$R^3O—[G]_p \quad (II)$$

where $R^3$ is an alkyl and/or alkenyl group containing 4 to 22 carbon atoms, G is a sugar unit containing 5 or 6 carbon atoms and p is a number of 1 to 10.

They may be obtained by the relevant methods of preparative organic chemistry, for example by acid-catalyzed acetalization of glucose with fatty alcohols.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The index p in general formula (II) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view.

The alkyl or alkenyl group $R^3$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred. In addition, the alkyl or alkenyl group $R^3$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12/14}$ coconut oil fatty alcohol having a DP of 1 to 3 are preferred.

Fatty Acid N-alkyl Polyhydroxyalkylamides

Fatty acid N-alkyl polyhydroxyalkylamides, which are also suitable as emulsifier component (c), are nonionic surfactants which correspond to formula (III):

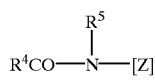

(III)

where $R^4CO$ is an aliphatic acyl group containing 6 to 22 carbon atoms, $R^5$ is an alkyl or hydroxyalkyl group containing 1 to 4 carbon atoms and [Z] is a linear or branched polyhydroxyalkyl group containing 3 to 12 carbon atoms and 3 to 10 hydroxyl groups. The fatty acid N-alkyl polyhydroxyalkylamides are known compounds which may normally be obtained by reductive amination of a reducing sugar with an alkylamine or an alkanolamine and subsequent acylation with a fatty acid, a fatty acid alkyl ester or a fatty acid chloride. Processes for their production are described in U.S. Pat. No. 1,985,424, in U.S. Pat. No. 2,016,962 and in U.S. Pat. No. 2,703,798 and in International patent application WO 92/06984. An overview of this subject by H. Kelkenberg can be found in Tens. Surf. Det. 25, 8 (1988).

The fatty acid N-alkyl polyhydroxyalkylamides are preferably derived from reducing sugars containing 5 or 6 carbon atoms, more particularly from glucose. Accordingly, the preferred fatty acid N-alkyl polyhydroxyalkylamides are fatty acid N-alkyl glucamides which correspond to formula (IV):

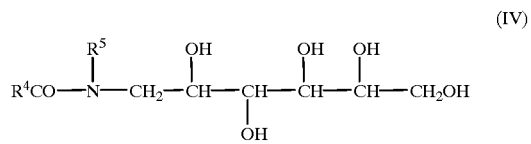

(IV)

Preferred fatty acid N-alkyl polyhydroxyalkylamides are glucamides corresponding to formula (IV) in which $R^5$ is an alkyl group and $R^4CO$ represents the acyl component of caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, arachic acid, gadoleic acid, behenic acid or erucic acid or technical mixtures thereof. Fatty acid N-alkyl glucamides (IV) obtained by reductive amination of glucose with methylamine and subsequent acylation with lauric acid or $C_{12/14}$ cocofatty acid or a corresponding derivative are particularly preferred. In addition, the polyhydroxyalkylamides may also be derived from maltose and palatinose.

Alkyl Ether Sulfates

Besides the nonionic glucosides or glucamides, anionic surfactants of the alkyl ether sulfate type may also be used as emulsifier component (c). It is known that alkyl ether sulfates ("ether sulfates") are anionic surfactants which are industrially produced by the sulfation of oxoalcohol or fatty alcohol polyglycol ethers with $SO_3$ or chlorosulfonic acid (CSA) and subsequent neutralization. Ether sulfates suitable for the purposes of the invention correspond to formula (V):

$$R^6O-(CH_2CH_2O)_xSO_3X \qquad (V)$$

in which $R^6$ is a linear or branched alkyl and/or alkenyl group containing 6 to 22 carbon atoms, x is a number of 1 to 10 and X is an alkali metal and/or alkaline earth metal, ammonium, alkylammonium, alkanolammonium or glucammonium. Typical examples are the sulfates of addition products of on average 1 to 10 and, more particularly, 2 to 5 moles of ethylene oxide with caproic alcohol, caprylic alcohol, 2-ethyl hexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol and technical mixtures thereof in the form of their sodium and/or magnesium salts. The ether sulfates may have both a conventional homolog distribution and a narrow homolog distribution. It is particularly preferred to use ether sulfates based on adducts of, on average, 2 to 3 moles of ethylene oxide with technical $C_{12/14}$ or $C_{12/18}$ cocofatty alcohol fractions in the form of their sodium and/or magnesium salts.

Betaines

Finally, betaines are suitable as the emulsifiers forming component (c) for stabilizing the pearlescent formulations according to the invention. Betaines are known surfactants which are mainly produced by carboxyalkylation, preferably carboxymethylation, of aminic compounds. The starting materials are preferably condensed with halocarboxylic acids or salts thereof, more particularly with sodium chloroacetate, 1 mole of salt being formed per mole of betaine. The addition of unsaturated carboxylic acids, for example acrylic acid, is also possible. Particulars of the nomenclature and, in particular, the distinction between betaines and "genuine" amphoteric surfactants can be found in the article by U. Ploog in Seifen-Öle-Fette-Wachse, 198, 373 (1982). Other reviews of this subject have been published, for example, by A. O'Lenick et al. in HAPPI, Nov. 70 (1986), by S. Holzman et al. in Tens. Surf. Det. 23, 309 (1986), by R. Bibo et al. in Soap Cosm. Chem. Spec., Apr. 46 (1990) and by P. Ellis et al. in Euro Cosm. 1, 14 (1994). Examples of suitable betaines are the carboxyalkylation products of secondary and, in particular, tertiary amines corresponding to formula (VI):

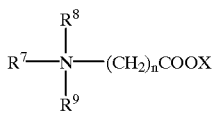

(VI)

in which $R^7$ stands for alkyl and/or alkenyl groups containing 6 to 22 carbon atoms, R8 stands for hydrogen or alkyl groups containing 1 to 4 carbon atoms, $R^9$ stands for alkyl groups containing 1 to 4 carbon atoms, n is a number of 1 to 6 and X is an alkali metal and/or alkaline earth metal or ammonium. Typical examples are the carboxymethylation products of hexyl methyl amine, hexyl dimethyl amine, octyl dimethyl amine, decyl dimethyl amine, dodecyl methyl amine, dodecyl dimethyl amine, dodecyl ethyl methyl amine, $C_{12/14}$ cocoalkyl dimethyl amine, myristyl dimethyl amine, cetyl dimethyl amine, stearyl dimethyl amine, stearyl ethyl methyl amine, oleyl dimethyl amine, $C_{16/18}$ tallow alkyl dimethyl amine and technical mixtures thereof.

Other suitable betaines are carboxyalkylation products of amido-amines corresponding to formula (VII):

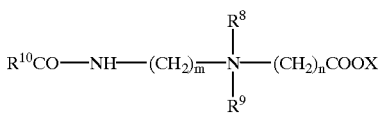

(VII)

in which $R^{10}CO$ is an aliphatic acyl group containing 6 to 22 carbon atoms and 0 or 1 to 3 double bonds, m is a number of 1 to 3 and $R^8$, $R^9$, n and X are as defined above. Typical examples are reaction products of fatty acids containing 6 to 22 carbon atoms, namely caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and technical mixtures thereof, with N,N-dimethyl aminoethyl amine, N,N-dimethyl aminopropyl amine, N,N-diethyl aminoethyl amine and N,N-diethyl aminopropyl amine which are condensed with sodium chloroacetate. It is preferred to use a condensation product of $C_{8/18}$ cocofatty acid-N,N-dimethyl aminopropyl amide with sodium chloroacetate.

Other suitable starting materials for the betaines to be used in accordance with the invention are imidazolines. Imidazolines are also known compounds which may be obtained, for example, by cyclizing condensation of 1 or 2 moles of fatty acid with polyfunctional amines, for example aminoethyl ethanolamine (AEEA) or diethylene triamine. The corresponding carboxyalkylation products are mixtures of different open-chain betaines. Typical examples are condensation products of the above-mentioned fatty acids with AEEA, preferably imidazolines based on lauric acid or—again—$C_{12/14}$ cocofatty acid which are subsequently betainized with sodium chloroacetate.

Cosmetic Formulations

The percentage contents of components (a), (b) and (c) in the formulations according to the invention, based on their solids content, may be (1 to 15): (1 to 15): (70 to 98) parts by weight, with the proviso that the quantities add up to 100% by weight. In one preferred embodiment of the invention, the cosmetic formulations have the following composition:

(a) 0.1 to 5 and preferably 0.5 to 2% by weight dialkyl ethers corresponding to formula (I),
(b) 0.1 to 5 and preferably 1 to 2% by weight cationic polymers and
(c) 1 to 50 and preferably 5 to 25% by weight emulsifiers, with the proviso that the quantities add up to 100% by weight with water and other typical auxiliaries and additives.

Commercial Applications

The pearlescent formulations containing cationic polymers according to the invention are distinguished by high stability in storage and brilliant pearlescence. Since the combination of the selected pearlescers and selected emulsifiers is critical to the stability of the formulations, the present invention also relates to the use of the mixtures mentioned for the production of pearlescent conditioning shampoos.

Cosmetic formulations

The formulations according to the invention, such as for example hair shampoos, hair lotions, foam baths, cremes, lotions or emollients, may also contain other mild surfactants, oils, co-emulsifiers, superfatting agents, stabilizers, waxes, consistency regulators, thickeners, biogenic agents, anti-dandruff agents, film formers, preservatives, hydrotropes, solubilizers, UV filters, insect repellents, self-tanning agents, dyes and fragrances as further auxiliaries and additives.

Typical examples of suitable mild, i.e. particularly skin-compatible, surfactants are monoglyceride sulfates, mono- and/or dialkyl sulfosuccinates, fatty acid isethionates, fatty acid sarcosinates, fatty acid taurides, fatty acid glutamates, ether carboxylic acids and/or protein fatty acid condensates, the latter preferably being based on wheat proteins.

Suitable oils are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols, esters of linear $C_{6-22}$ fatty acids with branched alcohols, more particularly 2-ethyl hexanol, esters of linear and/or branched fatty acids with polyhydric alcohols (for example propylene glycol, dimer diol or trimer triol) and/or Guerbet alcohols, triglycerides based on $C_{6-10}$ fatty acids, esters of $C_{6-22}$ fatty alcohols and/or Guerbet alcohols with aromatic carboxylic acids, more particularly benzoic acid, vegetable oils, branched primary alcohols, substituted cyclohexanes, linear $C_{6-22}$ fatty alcohol carbonates, esters of benzoic acid with $C_{6-22}$ alcohols, Guerbet carbonates and/or aliphatic or naphthenic hydrocarbons.

Suitable co-emulsifiers are, for example, nonionic surfactants from at least one of the following groups:

(1) products of the addition of 2 to 30 moles of ethylene oxide and/or 0 to 5 moles of propylene oxide to linear fatty alcohols containing 8 to 22 carbon atoms, to fatty acids containing 12 to 22 carbon atoms and to alkylphenols containing 8 to 15 carbon atoms in the alkyl group;
(2) $C_{12/18}$ fatty acid monoesters and diesters of products of the addition of 1 to 30 moles of ethylene oxide to glycerol;
(3) glycerol monoesters and diesters and sorbitan monoesters and diesters of saturated and unsaturated fatty acids containing 6 to 22 carbon atoms and ethylene oxide adducts thereof;

(4) adducts of 15 to 60 moles of ethylene oxide with castor oil and/or hydrogenated castor oil;

(5) polyol esters and, in particular, polyglycerol esters such as, for example, polyglycerol polyricinoleate or polyglycerol poly-12-hydroxystearate. Mixtures of compounds from several of these classes are also suitable;

(6) products of the addition of 2 to 15 moles of ethylene oxide with castor oil and/or hydrogenated castor oil;

(7) partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);

(8) trialkyl phosphates and mono-, di- and/or tri-PEG-alkyl phosphates;

(9) wool wax alcohols;

(10) polysiloxane/polyalkyl polyether copolymers and corresponding derivatives;

(11) mixed esters of pentaerythritol, fatty acids, citric acid and fatty alcohol according to DE-PS 11 65 574 and/or mixed esters of fatty acids containing 6 to 22 carbon atoms, methyl glucose and polyols, preferably glycerol, and

(12) polyalkylene glycols.

The addition products of ethylene oxide and/or propylene oxide with fatty alcohols, fatty acids, alkylphenols, glycerol monoesters and diesters and sorbitan monoesters and diesters of fatty acids or with castor oil are known, commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide with glycerol are known as refatting agents for cosmetic formulations from DE-PS 20 24 051. Besides nonionic emulsifiers, cationic emulsifiers are also suitable, those of the esterquat type—especially methyl-quaternized difatty acid triethanolamine ester salts—being particularly preferred.

The superfatting agents used may be such substances as, for example, lanolin and lecithin and polyethoxylated or acylated lanolin and lecithin derivatives, polyol fatty acid esters, monoglycerides and fatty acid alkanolamides, the latter also serving as foam stabilizers. Suitable consistency regulators are, above all, fatty alcohols containing 12 to 22 and preferably 16 to 18 carbon atoms and, in addition, partial glycerides. These substances are preferably used in combination with alkyl oligoglucosides and/or fatty acid-N-methyl glucamides of the same chain length and/or polyglycerol poly-12-hydroxystearates. Suitable thickeners are, for example, polysaccharides, more particularly xanthan gum, guar guar, agar agar, alginates and tyloses, carboxymethyl cellulose and hydroxyethyl cellulose, relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols such as, for example, pentaerythritol or trimethylol propane, narrow-range fatty alcohol ethoxylates or alkyl oligoglucosides and electrolytes such as sodium chloride and ammonium chloride.

Typical examples of fats are glycerides while suitable waxes are inter alia beeswax, carnauba wax, candelilla wax, montan wax, paraffin wax or microwaxes, optionally in combination with hydrophilic waxes, for example cetostearyl alcohol, or partial glycerides. The pearlescent waxes used may be, in particular, mono- and difatty acid esters of polyalkylene glycols, partial glycerides or esters of fatty alcohols with polybasic carboxylic acids or hydroxycarboxylic acids. Suitable stabilizers are metal salts of fatty acids such as, for example, magnesium, aluminium and/or zinc stearates. Biogenic agents in the context of the invention are, for example, tocopherol, tocopherol acetate, tocopherol palmitate, ascorbic acid, retinol, bisabolol, allantoin, phytantriol, panthenol, AHA acids, plant extracts and vitamin complexes. Suitable anti-dandruff agents are Climbazol, Octopirox and zinc pyrithione. Typical film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

In the context of the invention, UV filters are organic compounds which are capable of absorbing ultraviolet rays and of releasing the energy absorbed in the form of longer wave radiation, for example heat. Typical examples are 4-aminobenzoic acid and esters and derivatives thereof (for example 2-ethylhexyl-p-dimethylaminobenzoate or p-dimethylaminobenzoic acid octyl ester), methoxycinnamic acid and derivatives thereof (for example 4-methoxycinnamic acid-2-ethylhexyl ester), benzophenones (for example oxybenzone, 2-hydroxy4-methoxybenzophenone), dibenzoyl methanes, salicylate esters, 2-phenyl benzimidazole-5-sulfonic acid, 1-(4-tert.butylphenyl)-3-(4'-methoxyphenyl)-propane-1,3-dione, 3-(4'-methyl)-benzylidenebornan-2-one, methylbenzylidene camphor and the like. Other suitable UV filters are finely disperse metal oxides and salts, for example titanium dioxide, zinc oxide, iron oxide, aluminium oxide, cerium oxide, zirconium oxide, silicates (talcum) and barium sulfate. The particles should have an average diameter of less than 100 nm, preferably from 5 to 50 nm and more preferably from 15 to 30 nm. They may be spherical in shape although ellipsoidal particles or other non-spherical particles may also be used. Besides the two above-mentioned groups of primary light filters, secondary light filters of the antioxidant type, which interrupt the photochemical reaction chain initiated when UV radiation penetrates into the skin, may also be used. Typical examples of these secondary light filters are Superoxid-Dismutase, Tocopherols (vitamin E) and ascorbic acid (vitamin C).

In addition, hydrotropes, such as, for example, ethanol, isopropyl alcohol or polyols may be used to improve flow behavior. Suitable polyols preferably contain 2 to 15 carbon atoms and at least two hydroxyl groups. Typical examples are glycerol;

alkylene glycols such as, for example, ethylene glycol, diethylene glycol, propylene glycol, butylene glycol, hexylene glycol and polyethylene glycols having an average molecular weight of 100 to 1,000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms such as, for example, sorbitol or mannitol;

sugars containing 5 to 12 carbon atoms such as, for example, glucose or sucrose and aminosugars such as, for example, glucamine.

Suitable preservatives are, for example, phenoxyethanol, formaldehyde solution, parabens, pentanediol or sorbic acid. Suitable insect repellents are N,N-diethyl-m-toluamide, pentane-1,2-diol or Insect Repellent 3535. A suitable self-tanning agent is dihydroxyacetone. Suitable dyes are any of the substances suitable and approved for cosmetic purposes as listed, for example, in the publication "Kosmetische Färbemittel" of the Farbstoffkommission der Deutschen Forschungs-gemeinschaft, Verlag Chemie, Weinheim, 1984, pages 81 to 106, These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular formulation. The formulations may be prepared by standard cold or hot processes and are preferably produced by the phase inversion temperature method.

EXAMPLES

The test formulations were stored for 14 days at 20° C. and were then subjectively evaluated for stability in storage and pearlescence. For stability in storage, (+++) means unchanged, (++) means barely noticeable clouding, (+) means distinct clouding and (−) means sedimentation of the cationic polymer. For pearlescence, (+++) means brilliant, (++) means moderately brilliant and (+) means dull. The conditioning effect was determined via the wet combability of hair tresses. To this end, the combing work in mV was measured for an untreated tress of hair and for an identical tress treated with the test solution. The result is expressed as the difference between these two values as the average of three determinations. The greater the difference, the more distinctly combing work is reduced and hence combability is improved. Dermatological compatibility was determined as the total irritation score against a standard formulation. The results are set out in Table 1. Formulations 1 to 4 correspond to the invention while formulations C1 and C2 are intended for comparison.

TABLE 1

Composition and Properties of Pearlescent Shampoos Containing Cationic Polymers

| INCI Name | 1 | 2 | 3 | 4 | C1 | C2 |
|---|---|---|---|---|---|---|
| Distearylether | 1.0 | 1.0 | 1.0 | 1.0 | — | 1.0 |
| Ethyleneglycol Distearate | — | — | — | — | 1.0 | — |
| Lauryldimonium Hydroxypropyl Hydrolyzed collagen | 2.0 | — | 2.0 | 2.0 | 2.0 | 2.0 |
| Quaternized Hydroxyethyl Cellulose | — | 2.0 | — | — | — | — |
| Lauryl Glucoside | 15.0 | — | — | 5.0 | — | — |
| Sodium Laureth Sulfate | — | 12.0 | 12.0 | 10.0 | 12.0 | — |
| Cocoamidopropyl Betaine | — | — | 5.0 | 2.0 | — | — |
| Laureth-2 | — | — | — | — | — | 30.0 |
| Water | | | to 100 | | | |
| Stability in storage | ++ | ++ | ++ | +++ | + | − |
| Pearlescence | +++ | +++ | +++ | +++ | ++ | + |
| Wet combability [mV] | 44 | 39 | 38 | 47 | 20 | 19 |

TABLE 1-continued

Composition and Properties of Pearlescent Shampoos Containing Cationic Polymers

| INCI Name | 1 | 2 | 3 | 4 | C1 | C2 |
|---|---|---|---|---|---|---|
| Skin-cosmetic compatibility [% rel.] | 105 | 104 | 107 | 109 | 102 | 100 |

What is claimed is:

1. A pearlescent composition comprising:

(a) a dialkyl ether corresponding to formula (I):

$$R^1\text{—}O\text{—}R^2 \quad (I)$$

wherein $R^1$ and $R^2$ independently of one another represent a member selected from the group consisting of a linear or branched alkyl group having from 12 to 22 carbon atoms and a linear or branched alkenyl group having from 12 to 22 carbon atoms, (b) a cationic polymer selected from the group consisting of cationic cellulose derivatives, cationic starches, copolymers of diallyl ammonium salts and acrylamides, quaternized vinyl pyrrolidone/vinyl imidazole polymers, condensation products of polyglycols and amines, quaternized collagen polypeptides, quaternized wheat polypeptides, polyethylenelmines, copolymers of adipic acid and dimethylaminohydroxypropyl diethylenetriamine, copolymers of acrylic acid with dimethyl diallyl ammonium chloride, polyaminopolyamides, cationic chitin derivatives, condensation products of dihaloalkyls with bis-dialkylamines, quaternized ammonium salt polymers, and mixtures thereof; and (c) an alkyl ether sulfate emulsifier.

2. The composition of claim 1 wherein the dialkyl ether is distearyl ether.

3. The composition of claim 1 wherein the emulsifier is an alkyl ether sulfate corresponding to formula (V):

$$R^6O\text{—}(CH_2CH_2O)_xSO_3X \quad (V)$$

wherein $R^6$ is a linear or branched alkyl and/or alkenyl group containing from 6 to 22 carbon atoms, x is a number from 1 to 10, and X is selected from the group consisting of an alkali metal, an alkaline earth metal, ammonium, alkylammonium, alkanolammonium and glucammonium.

4. The composition of claim 1 containing from 1 to 15% by weight of the dialkyl ether, from 1 to 15% by weight of the cationic polymer, and from 70 to 98% by weight of the emulsifier, all weights being based on the total weight of the composition.

5. The composition of claim 1 wherein the dialkyl ether has an average particle size of from 0.1 to 20 Fm.

6. A cosmetic composition comprising:

(a) from 0.1 to 5% by weight of a dialkyl ether corresponding to formula (I):

$$R^1\text{—}O\text{—}R^2 \quad (I)$$

wherein $R^1$ and $R^2$ independently of one another represent a member selected from the group consisting of a linear or branched alkyl group having from 12 to 22 carbon atoms and a linear or branched alkenyl group having from 12 to 22 carbon atoms;

(b) from 0.1 to 5% by weight of a cationic polymer selected from the group consisting of cationic cellulose derivatives, cationic starches, copolymers of diallyl ammonium sails and acrylamides, quaternized vinyl pyrrolidone/vinyl imidazole polymers, condensation products of polyglycols and amines, quaternized collagen polypeptides, quaternized wheat polypeptides, polyethyleneimines, copolymers of adipic acid arid dimethylaminohydroxypropyl diethylenetriamine, copolymers of acryl a acid with dimethyl diallyl ammonium chloride, polyaminopolyamides, cationic chitin derivatives, condensation products of dihaloalkyls with bis-dialkylamines, quaternized ammonium salt polymers, and mixtures thereof;

(c) from 1 to 50% by weight of an alkyl ether sulfate emulsifier; and (d) remainder, water, all weights being based on the total weight of the cosmetic composition.

7. A process for imparting pearlescent properties to a cosmetic composition comprising adding a pearlescent-effective amount of the pearlescent composition of claim 1 to the cosmetic composition.

8. The process of claim 7 wherein the cosmetic composition is selected from the group consisting of a hair shampoo, a hair lotion, a foam bath, and a skin creme.

* * * * *